US00PP16809P3

(12) United States Plant Patent
Hofmann

(10) Patent No.: US PP16,809 P3
(45) Date of Patent: Jul. 11, 2006

(54) **NEW GUINEA *IMPATIENS* PLANT NAMED 'FISUPNIC TALLRED'**

(50) Latin Name: *Impatiens hawkeri*
Varietal Denomination: Fisupnic Tallred

(75) Inventor: Birgit C. Hofmann, Bendorf (DE)

(73) Assignee: Florfis AG, Binningen (CH)

( * ) Notice: Subject to any disclaimer, the term of this patent is extended or adjusted under 35 U.S.C. 154(b) by 41 days.

(21) Appl. No.: 10/829,348

(22) Filed: Apr. 22, 2004

(65) Prior Publication Data

US 2004/0216205 P1 Oct. 28, 2004

(30) Foreign Application Priority Data

Apr. 22, 2003 (CH) ..... 03-1999

(51) Int. Cl.
*A01H 5/00* (2006.01)

(52) U.S. Cl. ..... Plt./318

(58) Field of Classification Search ..... Plt./318
See application file for complete search history.

(56) References Cited

U.S. PATENT DOCUMENTS

PP13,226 P2 * 11/2002 Hofmann ..... Plt./318
PP13,703 P2 * 4/2003 Hofmann ..... Plt./318

* cited by examiner

*Primary Examiner*—Howard J. Locker
(74) *Attorney, Agent, or Firm*—Foley & Lardner LLP

(57) ABSTRACT

A new and distinct cultivar of New Guinea *Impatiens* plant named 'Fisupnic Tallred', particularly characterized by the combined features of brilliant red (with orange-red tones) flower color; relatively large, round, flat flower shape; intense green foliage; vigorous growth, well-branched, wide and rounded plant habit; early to medium flowering response; and suitable for tubs and as outdoor bedding plants.

1 Drawing Sheet

Genus and species of the plant claimed: *Impatiens hawkeri.*

Variety denomination: 'Fisupnic Tallred'.

BACKGROUND OF THE INVENTION

The present invention comprises a new and distinct cultivar of New Guinea *Impatiens,* botanically known as *Impatiens hawkeri,* and hereinafter referred to by the cultivar name 'Fisupnic Tallred'.

'Fisupnic Tallred' is a product of a planned breeding program and originated from a hybridization made by the inventor, Birgit C. Hofmann, in a controlled breeding program in Hillscheid, Germany, in the summer of 2000.

The female parent was the variety 'Fisimp 100' (unpatented), characterized by red flowers, medium green foliage, and vigorous growth habit.

The male parent was the variety 'Fisimp 171' (U.S. Plant Pat. No. 13,703), characterized by dark red and reddish-purple flower color, deep green foliage, and medium sized plant habit.

'Fisupnic Tallred' was discovered and selected as a flowering plant within the progeny of the stated cross made by the inventor in April, 2001, in a greenhouse in Galdar, Can Canaria, Spain.

The first act of vegetative or asexual reproduction of 'Fisupnic Tallred' was accomplished when cuttings were taken from the initial selection in July, 2001, in a controlled environment in Galdar, Gran Canaria, Spain, by, or under the supervision of, Birgit Hofmann.

Horticultural examination of plants grown from these cuttings initiated in the spring of 2002, in Hillscheid, Germany, and continuing thereafter, has demonstrated that the combination of characteristics as herein disclosed for 'Fisupnic Tallred' are firmly fixed and are retained through successive generations of asexual reproduction. The new cultivar reproduces true to type.

'Fisupnic Tallred' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany, under green-house conditions which approximate those generally used in commercial practice.

BRIEF SUMMARY OF THE INVENTION

The following traits have been repeatedly observed and are determined to be basic characteristics of 'Fisupnic Tallred', which in combination distinguish this *Impatiens* as a new and distinct cultivar:

1. Brilliant red (with orange-red tones) flower color;
2. relatively large, round, flat flower shape;
3. intense green foliage;
4. vigorous growth, well-branched, wide and rounded plant habit;
5. early to medium flowering response; and
6. suitable for tubs and as outdoor bedding plants.

Of the many commercial cultivars known to the inventor, the most similar in comparison to 'Fisupnic Tallred' is the patented variety 'Fisnics Red' (U.S. Plant Pat. No. 13,226), and the parental variety 'Fisimp 171'.

In comparison to 'Fisnics Red', 'Fisupnic Tallred' has somewhat larger flowers (larger diameter by 5 mm) and a medium red (with red-orange tones)—flower color (RHS 44A to RHS 45A), while 'Fisnics Red' has a darker red flower color (RHS 45A to RHS 46B, fading to RHS 46B and RHS 46C), slightly deeper green foliage color, larger leaves, and generally taller plant habit (taller in height by 7.5 cm).

In comparison to the parental variety 'Fisimp 171', 'Fisupnic Tallred' has a medium red (with orange-red tones) flower color (RHS 44A to RHS 45A), while 'Fisimp 171' has a darker red and somewhat reddish-purple flower color (RHS 46B and RHS 57B, fading to 57D). 'Fisupnic Tallred' has a medium green foliage color, not quite as deep green as 'Fisimp 171', and 'Fisupnic Tallred' has mainly green stems, while 'Fisimp 171' has red-purple branches.

BRIEF DESCRIPTION OF THE DRAWINGS

The accompanying photographic drawing shows typical flower and foliage characteristics of 'Fisupnic Tallred' with colors being as true as possible with illustrations of this type. The photographic drawing shows a side view of a typical flowering plant of 'Fisupnic Tallred'.

DETAILED BOTANICAL DESCRIPTION

In the following description color references are made to The Royal Horticultural Society Colour Chart (R.H.S.). The color values were determined indoors from plants growing in a greenhouse in May 2003, Hillscheid, Germany. The description is based on plants which were planted as rooted cuttings in 12 cm pots in late February 2003, and then grown in a greenhouse at a minimum temperature of 16° C. Most observations and measurements were made after the beginning of flowering in mid May, when the plants were about 12 weeks old.

Plant:

*General appearance and form.*—Plant habit: Tall, uniformly mounded, well-branched (self-branching), but only moderately tight; growth is indeterminate, though weak after begin of flowering. Height: 20.0 cm. Width: 37.5 cm. Number of branches: Approximately 12. Internode length: 40–55 mm. Length of braches: 14–16 cm. Diameter of branches: 6–8 mm. Stem color: Mainly light green, RHS 145 B–C, brownish at the nodes. Propagation: Terminal shoot tips for cuttings. Rooting: Roots initiate in about 18 days at 22° C., from sticking to transplanting. Cultivation time: To produce a marketable flowering plant in a 12 cm pot takes about 10 weeks of growing time.

Foliage:

*Arrangement.*—Primarily in whorls.

*Shape.*—Elliptic, with acute base and acute to acuminate tip, surface somewhat rippled, most often glossy.

*Margin.*—Serrulated, ciliated.

*Length.*—11.3 cm.

*Width.*—4.0 cm.

*Upper surface, main color.*—Deep medium green, no variegation; Mature leaves RHS 137 A; young leaves between RHS 141 B and RHS 141 C.

*Lower surface, main color.*—Light green, about RHS 138 B (both mature and young leaves.

*Veins on upper surface, color.*—Pale green, RHS 145 A.

*Veins on lower surface, Color.*—Pale green, between RHS 145 B to RHS 145 C.

*Petiole.*—25–30 mm in length, 3 mm in diameter; upper side color RHS 48B, lower side RHS 145 C.

Inflorescence:

*Flowering response.*—9–10 weeks after planting of rooted cuttings.

*Flowering season.*—Generally from March to October, depending on light intensity.

*Flower.*—Number of flowers per and arrangement per lateral branch: Usually 6–8 flowers and flower buds, in various stages of development. Flowers appear at the upper nodes and at the terminal node and are positioned above and beyond the foliage and typically face upward or outward.

*Flower longevity.*—Flowers last about 8 to 9 days on the plant.

*Fragrance.*—Flowers not fragrant.

*Form of corolla.*—Single-type, 5 petals.

*Shape of corolla.*—Nearly round, with the petals overlapping, almost flat.

*Average length.*—75 mm.

*Average width.*—72 mm.

*Shape of petals.*—Cordate, at the top end weak to moderate lobes, top petal 28 mm long, 44 mm wide; lateral petals 32 mm long, 33 mm wide; lower petals 30 mm long, 40 mm wide.

*Texture.*—Smooth, velvety.

*Aspect.*—Flat.

*Color* (*general tonality from a distance of three meters*).—Uniform, brilliant red.

*Color of upper surface.*—Red, between RHS 44 A and 45 A (including eye zone).

*Color of lower surface.*—Orange-red, RHS 43 B.

*Spur color.*—Deep pink, closest to RHS 53 C (red group).

*Spur shape and size.*—Downwardly curved, about 70 mm long, 3 mm in diameter at the flower end.

*Pedicel color.*—Light green, RHS 145 B, partly brownish infused, RHS 179 B.

*Pedicel length.*—50–55 mm, 2 mm in diameter.

*Flower bud.*—Ovoid shape, 23 mm in length, 15 mm in diameter; color RHS 45 C.

Reproductive organs:

*Androecium.*—Stamens: 5 in number, fused, upper surface color is RHS 43 C Anthers: Fused, hooded. Pollen: Moderate (typical), whitish-yellow, about RHS 8 D.

*Gynoecium.*—Style and stigma: Five in number, very short, near RHS 150 D. Ovary: 5-celled, 5 mm long, surface color green RHS 137 A.

*Seed/fruit.*—Seed and fruit development have not been observed.

Disease/pest resistance/susceptibility:

Disease/pest resistance/susceptibility: plants of the new *Impatiens* cultivar have not been observed to be resistant or more susceptible to pathogens and pests common to *Impatiens*.

I claim:

1. A new and distinct cultivar of New Guinea *Impatiens* plant named 'Fisupnic Tallred' as described and illustrated herein.

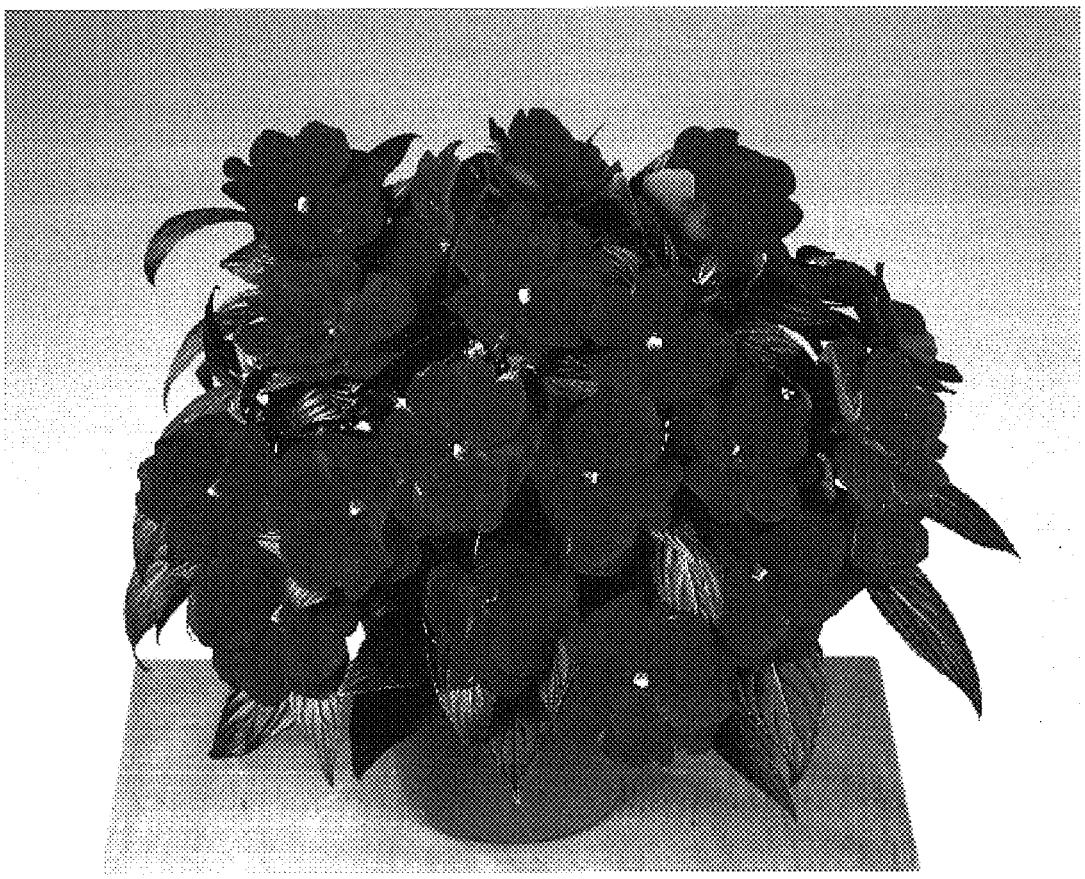

* * * * *